(12) United States Patent
Klatt et al.

(10) Patent No.: US 7,109,362 B2
(45) Date of Patent: Sep. 19, 2006

(54) PROCESS FOR THE PREPARATION OF LIPOIC ACID AND DIHYDROLIPOIC ACID

(75) Inventors: Martin Jochen Klatt, Bad Dürkheim (DE); Markus Niebel, Mannheim (DE); Joachim Paust, Neuhofen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 2 days.

(21) Appl. No.: 10/432,455

(22) PCT Filed: Nov. 29, 2001

(86) PCT No.: PCT/EP01/13955

§ 371 (c)(1),
(2), (4) Date: May 21, 2003

(87) PCT Pub. No.: WO02/44163

PCT Pub. Date: Jun. 6, 2002

(65) Prior Publication Data

US 2005/0101669 A1  May 12, 2005

(30) Foreign Application Priority Data

Nov. 30, 2000 (DE) .................. 100 59 718

(51) Int. Cl.
C07B 45/00 (2006.01)
A61K 31/095 (2006.01)
C07D 339/04 (2006.01)

(52) U.S. Cl. ............. 554/87; 514/440; 514/557; 424/401; 549/39; 562/512; 252/183.11; 252/183.13

(58) Field of Classification Search ........... 562/470, 562/512, 507; 252/183.11, 183.13
See application file for complete search history.

(56) References Cited

U.S. PATENT DOCUMENTS

| 5,530,143 | A | 6/1996 | Balkenhohl et al. |
| 5,693,664 | A | 12/1997 | Wessel et al. |
| 5,728,735 | A | 3/1998 | Ulrich et al. |
| 6,441,024 | B1 | 8/2002 | Klatt et al. |
| 6,906,210 | B1 * | 6/2005 | Klatt et al. ............ 554/87 |

FOREIGN PATENT DOCUMENTS

| DE | 41 36 773 | | 5/1993 |
| DE | 43 43 592 | | 6/1995 |
| DE | 43 43 593 | | 6/1995 |
| EP | 0487 986 | * | 6/1992 |
| EP | 487 986 | | 6/1992 |
| EP | 543 088 | | 5/1993 |
| EP | 487 986 | | 6/1995 |
| EP | 812 590 | | 12/1997 |
| WO | 00/08012 | | 2/2000 |
| WO | 00/24734 | | 5/2000 |
| WO | 00/53601 | | 9/2000 |
| WO | 00/59899 | | 10/2000 |

OTHER PUBLICATIONS

Rao et al, Synthetic Communications, 17(11) pp. 1339-1347 (1987).*
XP-001063331, Bringmann et al.
Short and Productive Syntheses..Bringmann etal.655-661.
Bio.MedChem,vol. 5 No. 2,253-261,1997, Adger et al.
J.Sci.Ind.Res.,vol. 49,8/90, 440-409, Yadav et al.
Tet.Ltrs.,vol. 30,No. 42,5705-5708,1989, Gopalan et al.
JP 8814/64 Abst. 1960-24703.
Synthetic Comm.,17(11) ,1339-1347(1987) Rao et al.
J.Chem.Soc.Perkin Trans,1988,9-12,1988, Brookes et al.
TetrahydronLett,28 1987, 19, 2183-2186,Rao et al.
Chem.Comm. 1983, 1051-1053, Brookes et al.

* cited by examiner

*Primary Examiner*—Rosalynd Keys
(74) *Attorney, Agent, or Firm*—Novak, Druce & Quigg, LLP

(57) ABSTRACT

The present invention relates to a process for the preparation of R- and S-lipoic acid and R- and S-dihydrolipoic acid comprising (a) reaction of

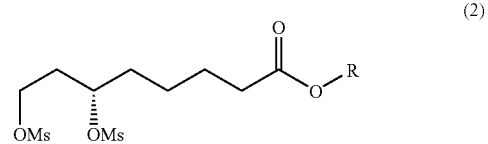

where
MS is $SO_2$—R' and R and R' independently of one another are $C_1$–$C_6$-alkyl, $C_3$–$C_8$-cycloalkyl, $C_3$–$C_8$-cycloalkylalkyl, aryl or aralkyl, with sodium sulfide and sulfur in methanol. The invention especially relates to processes for preparing pure R- or S-dihydrolipoic acid, which is either used directly or processed further to give R- and S-lipoic acid. The process also serves for the production of pharmaceuticals. The present invention further relates to a solution of sodium sulfide trihydrate and sulfur in methanol, the sulfur being present in a molar excess over the sodium sulfide trihydrate, and a kit which comprises the solution according to the invention.

20 Claims, No Drawings

PROCESS FOR THE PREPARATION OF LIPOIC ACID AND DIHYDROLIPOIC ACID

This application is submitted under 35 U.S.C. 371 and is the National Stage of International Application PCT/EP01/13955, filed Nov. 29, 2001.

Dihydrolipoic acid and lipoic acid are naturally occurring substances which have particular importance in cell metabolism. As a coenzyme, e.g. of pyruvate dehydrogenase, R-lipoic acid plays a central role in energy production. In order to fully display its very good antioxidative properties, R-Lipoic acid is activated to dihydrolipoic acid in the metabolism. R-Lipoic acid positively affects age-related changes in the metabolism and is therefore also of interest in the cosmetic field.

The references
Bringmann, Z. Naturforschung 1999, 54b, 665–661;
Adger, Bioorg. Med. Chem. 1997, 5, 253–61;
Yadav, J. Scientific & Industrial Res. 1990, 49, 400–409;
Gopalan, Tetrahedron Lett 1989, 42, 5705;
Rao, Synth. Commun. 17, 1987a, 11, 1339–1347
Rao, Tetrahedron Lett. 28, 1987b, 19, 2183–2186
Brookes, Perkin Transaction I, 1988, 9–12;
Brookes, Chemical Communication 1983, 1051–53; and
JP 1960-35704; EP 543088; EP 487 986;

disclose various methods for the preparation of optically pure R- and S-lipoic acid or dihydrolipoic acid.

The enantiomerically pure lipoic acid and dihydrolipoic acid are thus prepared in various ways such as chemical or enzymatic cleavage of the racemate, with the aid of chiral templates, by enantioselective synthesis or microbiological transformation.

The syntheses of R-lipoic acid and R-dihydrolipoic acid are described by way of example below. The S enantiomers in each case can also be prepared analogously.

Bringmann et al. propose two synthesis routes for R-lipoic acid, which start from chiral 6,8-dihydroxyoctanoic acid esters (1).

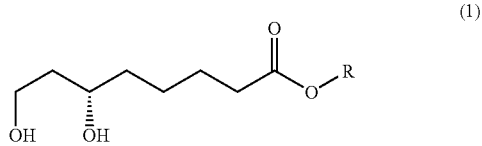

(1)

The yields of lipoic acid with respect to (1) are 65%; on introduction of sulfur using KSAc, the material obtained, however, has only a purity in the GC of 98%, which could be problematical for human applications.

Alternatively, according to Bringmann et al., the introduction of sulfur can be carried out in DMF using NaS+S, it being possible to carry out the subsequent hydrolysis using lipase or potassium carbonate. The methyl lipoate intermediately formed is very sensitive to polymerization.

Rao, 1987a, and 1987b describe the introduction of sulfur into the mesylate of the 6,8-dihydroxyoctanoic acid ester (1) using NaS+S in DMF in a yield of 70%.

The published syntheses either proceed via many steps and/or use expensive starting materials or reaction conditions. From yield, environmental and/or cost considerations, the known processes are worthy of improvement. Since lipoic acid and dihydrolipoic acid are also to be employed in humans, products which are as pure as possible and which can be prepared simply in high yields are desired.

The technical problem which thus underlies the present invention is therefore of making available a process by which lipoic acid and dihydrolipoic acid can be obtained in yields which are as high as possible and in high purity in an economically and ecologically advantageous manner.

The solution of the technical problem is made available by means of the embodiments described in the claims.

Consequently, the present invention relates to a process for the preparation of dihydrolipoic acid, comprising (a) reaction of

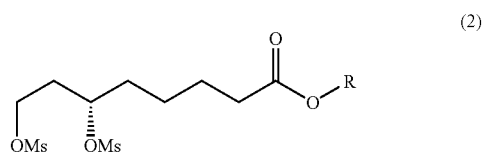

(2)

where
MS is $SO_2$—R' and R and R' independently of one another are $C_1$–$C_6$-alkyl, $C_3$–$C_8$-cycloalkyl, $C_3$–$C_8$-cycloalkylalkyl, aryl or aralkyl,
with sodium sulfide and sulfur in methanol.

The compound (2) is prepared, for example, by reaction of the corresponding alkyl 6,8-dihydroxyoctanoate (1) with triethylamine and mesyl chloride. The preferred alkyl esters are $C_1$–$C_6$-alkyl, and methyl is particularly preferred.

Aryl or Ar in aralkyl is preferably phenyl or naphthyl, which in each case can be substituted by one, two or three $C_1$–$C_4$-alkyl radicals; "alkyl" in aralkyl or cycloalkylalkyl is preferably $C_1$–$C_4$-alkyl, particularly preferably —$CH_2$—. The preferred meaning of Ms is mesylate or tosylate.

Surprisingly, the use of sodium sulfide and sulfur in methanol for the introduction of sulfur into (2) leads to essentially higher yields and purity in comparison with DMF. Thus only a yield of 70% to 75% is achieved in the use of sodium sulfide in DMF for the introduction of sulfur into (2) described in the prior art (Rao, 1987a; Examples). By means of the process according to the invention, a high chemical purity of R- or S-dihydrolipoic acid is achieved. Advantageously, however, not only the yield and purity of the products can be improved by the use of methanol as a solvent in the introduction of sulfur, but moreover also the preparation of dihydrolipoic acid by the process according to the invention can be simplified and cost-saving production can be made possible: methanol is a more inexpensive solvent than DMF.

Surprisingly, the process according to the invention is also suitable for the introduction of sulfur into other compounds.

Consequently, the invention also relates to a process for the preparation of compounds containing the structural element (3)

(3)

m = 0, 1
n = 0, 1 comprising the
(a) reaction of (4)

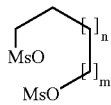

(4)

m = 0, 1
n = 0, 1 with sodium sulfide trihydrate and sulfur in methanol.

In one embodiment, the structural element (3) contains the substituents $R^1$, $R^2$, $R^3$ and $R^4$ (compound (3a)):

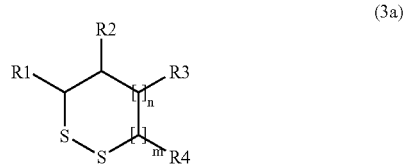

(3a)

m = 0, 1
n = 0, 1 where
$R^1$, $R^2$, $R^3$, and/or $R^4$, independently of one another, can be:
H;
unbranched or branched $C_1-C_{20}$-alkyl,
  where 0 to 3 carbon atoms can be replaced by O, S, NZ,
  and/or —$X^1$—(C=$X^2$)—,
  where $X^1$ is a bond, O, S or NZ,
  and/or $X^2$ is O, S, or NZ;
  and/or
a mono-, bi-, or tricyclic, aromatic, saturated or partially unsaturated $C_0-C_6$-alkylcarbo- or heterocycle having 3 to 17 carbon atoms,
  where 0 to 3 heteroatoms can be selected from S, N, and/or O;
  and where each carbon atom of the alkyl chains or of the ring can carry up to three of the following substituents OZ, SZ, (C=O)—OZ, NZZ$^1$, $C_1$ to $C_6$-alkyl;
  and where Z and/or $Z^1$ can be H or $C_1-C_6$-alkyl.
n+m is preferably 1 or 2.

The process according to the invention is also suitable for the preparation of derivatives of lipoic acid, dihydrolipoic acid and/or of (3), such as are described, for example, in DE 41 37 773, DE 43 43 592, DE 43 43 593, EP 812 590, WO 00/24734, WO 00/59899 and WO 00/53601 and which are included here. In particular, the salts, esters or amides of the compounds mentioned here, preferably of dihydrolipoic acid, lipoic acid or of the compound (3), or of the compounds listed in the references mentioned, are also included. Processes for the preparation of metabolites of lipoic acid or dihydrolipoic acid, such as bisnorlipoic acid or tetralipoic acid, are likewise included.

The reaction according to the invention of the sulfonic acid derivatives (2), e.g. of the mesylate, is preferably carried out in an $Na_2S/S$ mixture in methanol. The term "methanol" is understood as meaning methanolic solutions according to the invention, in which sodium sulfide, preferably the trihydrate, and sulfur dissolve well. The person skilled in the art knows how high the proportion of one or more other solvent(s) in the methanolic solution to and depends on the "other solvent(s)". Other solvent(s) is/are understood as meaning, for example, water, DMF, or other alcohols, e.g. ethanol, isopropanol, etc. The person skilled in the art can easily test, by means of a test series corresponding to the prior art whether a methanolic solution is suitable for the process according to the invention, in particular whether sodium sulfide, preferably sodium sulfide trihydrate, and sulfur dissolve well therein. Consequently, the methanolic solution consists of an at least 80% content by weight of methanol, a 90% content by weight is more preferred, particularly preferably a 95% content by weight of methanol, and more than 95% of methanol is most preferred. The preferred additive is water and/or ethanol. The methanolic mixture preferably contains at least equimolar amounts of $Na_2S$, S and mesylate and preferably a lower than a 100% molar excess each of $Na_2S$ and S with respect to mesylate. A 25 to 35% molar excess of $Na_2S$ and a 45 to 55% molar excess of sulfur over the mesylate is more preferred. The methanolic $Na_2S$/S mixture is preferably boiled beforehand.

In a preferred embodiment, the process according to the invention is carried out by reaction using sodium sulfide trihydrate. Surprisingly, the use of sodium sulfide having a low content of water of crystallization is particularly advantageous and leads to a very high yield in the process according to the invention. The use of the trihydrate is particularly advantageous compared with the nonahydrate hitherto employed in the literature or alternatively compared with anhydrous sodium sulfide. It is seen that sodium sulfide trihydrate leads to the highest yield of dihydrolipoic acid.

In a further embodiment, sulfur is present in the process according to the invention in a molar excess over the sodium sulfide, in particular the sodium sulfide trihydrate. In a preferred embodiment, a molar excess of 5 to 30% of sulfur over sodium sulfide is used. Preferably, an excess of sodium sulfide and sulfur over the mesylate is present. Thus in a particularly preferred embodiment, 1.3 equivalents of sodium sulfide and 1.5 equivalents of elemental sulfur can be used with respect to 1.0 equivalent of mesylate in methanol.

In a further embodiment, the process according to the invention comprises at least one further subsequent process step, selected from the group consisting of:
(b) reaction with a complex hydride;
(c) extraction of a protic solution of R-dihydrolipoic acid or S-dihydrolipoic acid with organic solvents at a pH of 9 to 10;
(d) extraction of R-dihydrolipoic acid or S-dihydrolipoic acid with organic solvents from a protic solution at a pH of 4 to 5; and
(e) distillation of the dihydrolipoic acid.

"Complex hydrides" are preferably understood as meaning borohydrides, in particular alkali metal borohydrides such as $NaBH_4$. The reaction with complex hydrides is preferably carried out in alkaline solution, particularly in concentrated alkali metal hydroxide solution. A borole solution (e.g. 12% strength $NaBH_4$ in 14M NaOH; the respective composition of the borole solution can vary depending on the manufacturer and batch) is particularly preferred.

If, after the reaction with a complex hydride, the protic solution of dihydrolipoic acid is extracted at a pH of 9 to 10, preferably at approximately 9.5, with an organic solvent, a greater yield of crystallizate is obtained after working up to give lipoic acid.

Protic solutions are understood as meaning solvent mixtures containing at least 30% of water, preferably more than 50% of water, particularly preferably more than 75% of water. The other components are polar solvents such as DMF or alcohols, in particular methanol. Organic solvents for the extraction are preferably apolar solvents, e.g. halogenated solvents such as methylene chloride or chloroform, glycol ethers, ethers such as diethyl ether or methyl t-butyl ether, esters such as ethyl acetate, aliphatic and aromatic hydrocarbons such as cyclohexane, hexane, heptane, toluene, or mixtures thereof, hexane, heptane, toluene and ethyl acetate being preferred as solvents.

If the protic solution of dihydrolipoic acid is extracted at a pH of 4 to 5, preferably at approximately 4.5, in organic solvent, after working up to give lipoic acid a greater yield of crystallizate is obtained. A distillation of the dihydrolipoic acid can follow this step.

Surprisingly, dihydrolipoic acid can be distilled without significant decomposition in a temperature range from 160 to 220° C., preferably even at 180 to 210° C., particularly preferably at 200° C.±5° C., at pressures of 0.5 to 5 mbar, particularly preferably at 1 to 3 mbar. The distillation is preferably carried out continuously (Sambay, falling-film or thin-layer evaporator). This pressure range can be realized industrially without considerable outlay. Surprisingly, after subsequent oxidation and crystallization over 10% more lipoic acid is obtained from the dihydrolipoic acid than without distillation. This further optimization of the purification of the dihydrolipoic acid surprisingly led, although more steps were introduced, to higher yields of pure lipoic acid. Surprisingly, it was also found that the reversal of the extraction steps (firstly extraction at pH 4 to 5 and subsequent purification at pH 9 to 10) makes possible high yields of lipoic acid crystallizate even without distillation of the dihydrolipoic acid. This procedure is likewise particularly preferred.

Preferably, the process according to the invention is carried out without isolation of the intermediates.

In a further preferred embodiment, in the process according to the invention sodium sulfide trihydrate and sulfur are added in methanol to (2) or (4). Surprisingly, sodium sulfide trihydrate and sulfur dissolve readily in methanol at room temperature and afford a clear, easily meterable liquid. Thus the process according to the invention can advantageously be carried out "inversely". The term "inversely" is understood here as meaning that the sulfur reagent consisting of sodium sulfide trihydrate and sulfur in methanol is added directly to the mesylate (2) or (4), preferably under a protective atmosphere, e.g. $N_2$. This particularly preferred process leads to a decreased contamination of the dihydrolipoic acid. The "inverse" procedure moreover causes an increase in yield for the preparation of lipoic acid to 85%. In terms of process technology, the inverse procedure additionally offers the advantage that the mesylate prepared beforehand no longer has to be drawn off from the vessel. The introduction of sulfur can be carried out as a one-pot reaction. When carrying out the process according to the invention, it is clear to the person skilled in the art that the yield and the occurrence of by-products depend on the manner of addition. Thus both too rapid an addition and too slow an addition can lead to increased formation of by-products. The person skilled in the art knows to adjust the respective addition rates and manner of addition to the reaction temperatures used, volumes, the preferred product quality, or the manner of mixing.

In a preferred embodiment, the reaction temperature for the process according to the invention is between room temperature and 70° C. A reaction temperature is particularly preferred which is between 35 and 45° C. Most preferred is a reaction temperature of 40° C. It has been found that under certain reaction conditions a reaction temperature of 40° C. leads to the highest yield. At temperatures which are too low; for example, a complete reaction cannot be achieved. The person skilled in the art knows to adjust the reaction temperature to the respective process conditions.

In a particularly preferred embodiment, the process according to the invention relates to the preparation of R-lipoic acid or S-lipoic acid, the process comprising an oxidation of the R- or S-dihydrolipoic acid. If the batch is acidified (e.g. pH<2) after preparation of the dihydrolipoic acid and extracted with an organic solvent (preferably ethyl acetate or toluene), a high yield of dihydrolipoic acid is obtained. If the dihydrolipoic acid obtained in this way is oxidized to lipoic acid and crystallized, very pure lipoic acid is obtained in high yield (GC>99.5%, ee HPLC (CSP)>99% (limit of detection)). The oxidation can be carried out, for example, using $FeCl_3$/air, the crystallization preferably in heptane/toluene (WO 00/08012).

The steps in the process indicated above for the purification of dihydrolipoic acid lead individually and in combination to higher yields of crystallized lipoic acid. The combination of individual steps is preferred and the carrying-out of all abovementioned process steps is very particularly preferred, in particular in the sequence as indicated in the examples.

The process according to the invention also comprises the preparation of R-dihydrolipoic acid or S-dihydrolipoic acid, the R-dihydrolipoic acid or S-dihydrolipoic acid being chemically pure. The preparation of chemically pure dihydrolipoic acid is preferably also included. Chemically pure lipoic acid or pure dihydrolipoic acid is understood as meaning chemically and, in particular, enantiomerically pure lipoic acid or dihydrolipoic acid. Chemically pure R-dihydrolipoic acid or S-dihydrolipoic acid and R-lipoic acid or S-lipoic acid is understood as meaning material which preferably has an enantiomeric purity (ee value determined by HPLC, CSP, preferably according to the process described in EP 694 542) of 70%, preferably 80%, particularly preferably 90%, very particularly preferably 95%, even more preferably 97% or 98%, most preferably 99% and greater, i.e. lying at the limit of detection. With respect to the chemical purity (GC or HPLC) of R- or S-dihydrolipoic acid, material having a purity of greater than or equal to 80%, particularly preferably greater than or equal to 90%, very particularly preferably greater than or equal to 95% or 97%, is particularly desired. With respect to the chemical purity of R- or S-lipoic acid, material preferably having greater than 99%, particularly preferably greater than 99.5%, very particularly preferably greater than 99.9%, purity is desired. This corresponds to the limit of detection of the methods used.

The process according to the invention also comprises the further processing of R-lipoic acid or S-lipoic acid into pharmacologically tolerable salts, or derivatives. Moreover, the invention relates to the further processing of R-lipoic acid or S-lipoic acid by the process according to the invention into pharmacologically tolerable derivatives such as esters or amides of lipoic acid. In addition, the invention also relates to the further processing of the R- or S-lipoic acid prepared according to the invention into pharmacologically tolerable salts, such as alkali metal and alkaline earth metal salts. The process according to the invention likewise relates to the preparation of metabolites, such as bisnorlipoic acid or tetranorlipoic acid, and their salts, esters or amides. The reaction and other derivatives are disclosed in the literature, e.g. in DE 43 43 592, 43 43 593, EP 812 590, WO 00/24734, WO 00/59899, WO 00/53601.

The invention also relates to a process for the production of cosmetics, of a pharmaceutical or pharmacon, comprising one of the steps of the process according to the invention, and (g) formulation of the R-dihydrolipoic acid, S-dihydrolipoic acid, R-lipoic acid or S-lipoic acid in a pharmacologically or dermatologically tolerable form.

Lipoic acid and dihydrolipoic acid can also be employed as nutraceuticals in the foodstuffs field. Use in cosmetics, as a pharmaceutical or pharmacon of dihydrolipoic acid and/or lipoic acid is also possible. It is known that R-lipoic acid increases the sensitivity to insulin and can thus be used as an antidiabetic, and also for the prevention and alleviation of diabetic long-term damage. Furthermore, lipoic acid or dihydrolipoic acid or derivatives can be employed for the treatment of glucose metabolic disorders (e.g. CNS) in insulin resistance, cancer and in hearing disorders.

In addition, the invention relates to a solution containing sodium sulfide trihydrate and sulfur in methanol, the sulfur being present in a molar excess. The term "methanol" is understood according to the invention as meaning methanolic solutions as defined above. The methanolic mixture preferably contains at least equimolar amounts of $Na_2S$ and S. The solution according to the invention, which can be prepared by dissolving $Na_2S.3H_2O$ and elemental sulfur in methanol at room temperature, offers significant advantages in comparison with the prior art: the reagent is a clear, readily meterable solution. It makes possible the "inverse procedure", in which for the first time the sulfur reagent can be added to the mesylate (2) or (4), which can lead to the reduction of oligomer formation. By means of the use of the solution, the introduction of sulfur can also be carried out at low temperatures, e.g. at 40° C. (formerly 65° C. or higher). The use of the solution according to the invention moreover leads to a simplification in terms of process technology, since the mesylate prepared beforehand can remain in the vessel. On account of the solution according to the invention, the introduction of sulfur can be carried out as a "one-pot reaction".

In a particularly preferred embodiment, the molar excess of sulfur in the solution according to the invention is between 5 and 30% relative to the sodium sulfide trihydrate. In a preferred embodiment, the solution according to the invention is employed in such a way that the ratio of mesylate, sodium sulfide and sulfur in the reaction mixture such as above is achieved.

In a further embodiment, the present invention also relates to a kit which contains the solution according to the invention. The solution can be packed in one or more containers. The constituents of the solution according to the invention, in particular sodium disulfide, preferably as the trihydrate, sulfur and methanol or a methanolic solution, can be packed separately or together in one container of the kit. The kit can be employed for carrying out the process according to the invention and can contain instructions for carrying it out.

Various documents are cited in the present text of this description. Each of the documents (including instructions and descriptions of manufacturers) are hereby included by the reference and by the description. This does not mean, however, that each of the documents mentioned is actually prior art for the present invention.

The present invention is illustrated by the following examples, without these in any manner being considered as restrictive.

EXAMPLES

Example 1

Synthesis of the 6,8-bismethanesulfonyloxyoctanoate

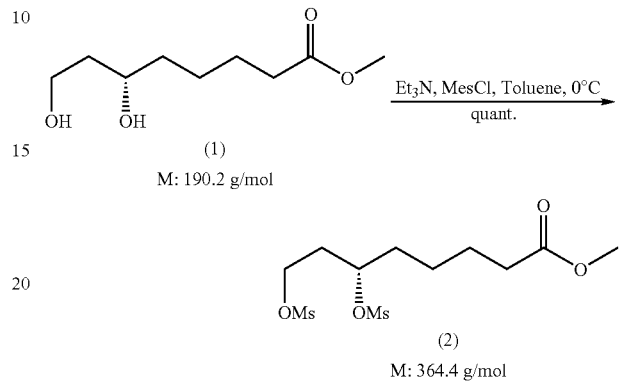

98 g (0.50 mol) of methyl 6,8-dihydroxyoctanoate were introduced into 1500 ml of toluene in a 2 l high-grade steel vessel at RT. The batch was cooled to 0° C. and treated with 173 ml (1.25 mol) of triethylamine. 143.2 g (1.25 mol) of methanesulfonyl chloride were added dropwise at an internal temperature of 0–5° C. in the course of 2 hours. The batch was then warmed to 25° C. and stirred for two hours.

For the separation of the triethylamine hydrochloride, 300 g of ice water were added to the reaction mixture and it was stirred intensively for 5 minutes. The aqueous phase was separated off and extracted once with toluene.

The combined toluene phases were washed once with completely deionized water and evaporated (pressure: 60 to 30 mbar, jacket temperature: 50° C., internal temperature: <45° C.). The crude solution is employed directly in the next stage.

Yield: 268.3 g of crude solution (conversion: quantitative)

Example 2

Introduction of Sulfur

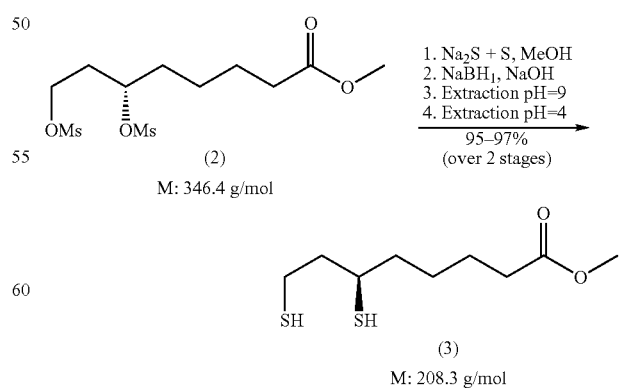

0.5 mol of the bismesylate solution was diluted with methanol and warmed to 40° C. A solution of 250 ml of methanol, 81.8 g (0.65 mol) of Na$_2$S.3H$_2$O and 24.0 g (0.75 mol) of sulfur were added dropwise at 40° C. under an N$_2$ atmosphere in the course of 4 hours. and the mixture was stirred for a further three hours.

1000 ml of completely deionized water are added and then 0.65 mol of borole solution, volatile material is distilled off and the mixture is stirred at this temperature for a further two hours.

The batch is treated with 100 ml of toluene and adjusted to pH 9 using H$_2$SO$_4$. The toluene phase is separated off and discarded.

The aqueous phase is treated with toluene and adjusted to pH 4.5 using H$_2$SO$_4$. After phase separation, the aqueous phase is reextracted once with toluene. The combined toluene phases are washed with completely deionized water and then evaporated in vacuo.

| Yield: | 125.7 g (96.6% with respect to diol 1) |
|---|---|
| Content (GC in stage): | 78% R-dihydrolipoic acid, 1.8% R-lipoic acid |

Example 3

Oxidation to lipoic acid

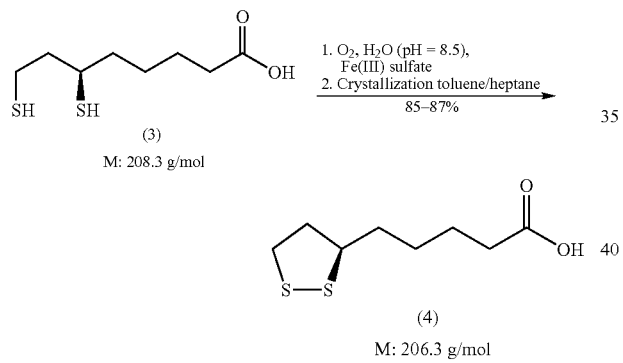

125.5 g of the dihydrolipoic acid solution are stirred in 5 l of completely deionized water in a 10 l round-bottomed flask, and the solution is adjusted to pH 8.5 using dilute sodium hydroxide solution and treated with catalytic amounts of Fe(III) sulfate solution. Air is introduced until the color lightens. After addition of 600 ml of toluene, the mixture is adjusted to pH 2 using H$_2$SO$_4$. The phases are separated and the water phase is extracted once with toluene. The combined toluene phases are concentrated to about 25% of the volume. The residue is treated with 600 ml of heptane, stirred under nitrogen and then forced through a filter loaded with silica gel. The filter is washed with toluene/heptane mixture.

The combined filtrates are inoculated into a 2 l high-grade steel vessel at room temperature. The batch is cooled and then stirred at –10° C. The yellow crystals are filtered off, washed with heptane and dried to constant weight.

| Yield: | 85.6% with respect to diol 1 |
|---|---|
| Content (GC in stage): | 99.95% |

| ee value: | >99%, it was not possible to detect the S-enantiomer |
|---|---|

It was additionally possible to detect 8.2% of R-lipoic acid in the mother liquor.

Example 4

(a) (1→2): 170 ml (1.25 mol) of triethylamine and a solution of 98 g (0.5 mol) of methyl (6S)-6,8-dihydroxyoctanoate 1 are introduced into 1 liter of toluene. The mixture is cooled and 143 g (1.25 mol) of mesyl chloride are added. After removal of the triethylammonium hydrochloride, the solution is concentrated. The conversion is quantitative.

(b) (2→3): 151 g (0.63 mol) of sodium sulfide and 24 g of sulfur powder are boiled in methanol. The reaction mixture is treated with 0.5 mol of the mesylate. It is diluted with completely deionized water. After reaction with 174 g (0.55 mol) of 12% NaBH$_4$ solution in 14 M sodium hydroxide solution (borole solution), the solvent is distilled off. The batch is adjusted to pH 1 and extracted with toluene.

Yield: 105.1 g (90%, 91% with respect to diol 1)

(c) (3→4): 105.1 g of dihydrolipoic acid are stirred in 5 liters of completely deionized water in a 10 liter round-bottomed flask, and the solution is adjusted to pH 8.5 and treated with catalytic amounts of Fe(III) chloride. Air is introduced until conversion is complete. The solution is adjusted to pH 2 and extracted with toluene. The phases are separated and the organic phase is concentrated. The residue is treated with technical grade heptane and forced through a filter loaded with 5 g of silica gel.

R-lipoic acid crystallizes with cooling and is dried in a stream of nitrogen.

The yield is 65.9 g (64% of theory with respect to diol 1).
GC content: >99.9%
ee content: >99%

Example 5

Introduction of the Distillation (a) (1→2): 170 ml (1.25 mol) of triethylamine and a solution of 98 g (0.5 mol) of methyl (6S)-6,8-dihydroxyoctanoate 1 are introduced into 1 liter of toluene. The mixture is cooled and 143 g (1.25 mol) of mesyl chloride are added. After removal of the triethylammonium hydrochloride, the solution is concentrated. The conversion is quantitative.

(b) (2→3): 151 g (0.63 mol) of sodium sulfide and 24 g of sulfur powder are boiled in methanol. The reaction mixture is treated with 0.5 mol of the mesylate. It is diluted with completely deionized water, 174 g (0.55 mol) of borole solution are added and the solvent is distilled off. The batch is adjusted to pH 1 and extracted with toluene. The organic phase is freed from the solvent. The residual oil is distilled in a falling-film evaporator (1 to 3 mbar, 200° C.). Yield: 95.3 g (96%, 88% with respect to diol 1).

(c) (3→4): 95.3 g of distilled dihydrolipoic acid are stirred in 5 liters of completely deionized water in a 10 liter round-bottomed flask, and the solution is adjusted to pH 8.5 and treated with catalytic amounts of Fe(III) chloride.

Air is introduced until conversion is complete. The solution is adjusted to pH 2 and extracted with toluene. The phases are separated and the organic phase is concentrated. The residue is treated with technical grade heptane and forced through a filter loaded with 5 g of silica gel. R-Lipoic acid crystallizes with cooling and is dried in a stream of nitrogen.

The yield is 74.2 g (72% of theory with respect to diol 1).
GC content: >99.9%
ee content: >99%

Example 6

Extraction at pH 9 and Distillation (a) (1→2): 170 ml (1.25 mol) of triethylamine and a solution of 98 g (0.5 mol) of methyl (6S)-6,8-dihydroxyoctanoate 1 are introduced into 1 liter of toluene. The mixture is cooled and 143 g (1.25 mol) of mesyl chloride are added. After removal of the triethylammonium hydrochloride, the solution is concentrated. The conversion is quantitative.

(b) (2→3): 151 g (0.63 mol) of sodium sulfide and 24 g of sulfur powder are boiled in methanol. The reaction mixture is treated with 0.5 mol of the mesylate. It is diluted with completely deionized water and 174 g (0.55 mol) of borole solution are added. The batch is adjusted to pH 9 using sulfuric acid and extracted with toluene. The toluene phase is discarded. The batch is then adjusted to pH 1 and extracted with toluene. The organic phase is freed from the solvent. The residual oil is distilled in a falling-film evaporator (1 to 3 mbar, 200° C.).
Yield: 91.1 g (95%, 85% with respect to diol 1).

(c) (3→4): 91.1 g of distilled dihydrolipoic acid are stirred in 5 liters of completely deionized water in a 10 liter round-bottomed flask, and the solution is adjusted to pH 8.5 and treated with catalytic amounts of Fe(III) chloride. Air is introduced until conversion is complete. The solution is adjusted to pH 2 and extracted with toluene. The phases are separated and the organic phase is concentrated. The residue is treated with technical grade heptane and forced through a filter loaded with 5 g of silica gel. R-Lipoic acid crystallizes with cooling and is dried in a stream of nitrogen.

The yield is 76.2 g (74% of theory with respect to diol 1)
GC content: >99.9%
ee content: >99%

Example 7

Extractions at pH 9, pH 4 and Distillation (a) (1→2): 170 ml (1.25 mol) of triethylamine and a solution of 98 g (0.5 mol) of methyl (6S)-6,8-dihydroxyoctanoate 1 are introduced into 1 liter of toluene. The mixture is cooled and 143 g (1.25 mol) of mesyl chloride are added. After removal of the triethylammonium hydrochloride, the solution is concentrated. The conversion is quantitative.

(b) (2→3): 151 g (0.63 mol) of sodium sulfide and 24 g of sulfur powder are boiled in methanol. The reaction mixture is treated with 0.5 mol of the mesylate. It is diluted with completely deionized water and 174 g (0.55 mol) of borole solution are added. The batch is adjusted to pH 9 using sulfuric acid and extracted with toluene. The toluene phase is discarded. The batch is then adjusted to pH 4 and extracted with toluene. The organic phase is freed from the solvent. The residual oil is distilled in a falling-film evaporator (1 to 3 mbar, 200° C.).
Yield: 95.2 g (97%, 88% with respect to diol 1).

(c) (3→4): 95.2 g of distilled dihydrolipoic acid are stirred in 5 liters of completely deionized water in a 10 liter round-bottomed flask, and the solution is adjusted to pH 8.5 and treated with catalytic amounts of Fe(III) chloride. Air is introduced until conversion is complete. The solution is adjusted to pH 2 and extracted with toluene. The phases are separated and the organic phase is concentrated. The residue is treated with technical grade heptane and forced through a filter loaded with 5 g of silica gel. R-Lipoic acid crystallizes with cooling and is dried in a stream of nitrogen.

The yield is 77.2 g (75% of theory with respect to diol 1)
GC content: >99.9%
ee content: >99%

Example 8

Extractions at pH 4, pH 9

(a) (1→2): 170 ml (1.25 mol) of triethylamine and a solution of 98 g (97%, 0.5 mol) of methyl (6S)-6,8-dihydroxyoctanoate 1 are introduced into 1 liter of toluene. The mixture is cooled and 143 g (1.25 mol) of mesyl chloride are added. After removal of the triethylammonium hydrochloride, the solution is concentrated. The conversion is quantitative.

(b) (2→3): 151 g (0.63 mol) of sodium sulfide and 24 g of sulfur powder are boiled in methanol. The reaction mixture is treated with 0.5 mol of the mesylate. It is diluted with completely deionized water and 174 g (0.55 mol) of borole solution are added. The batch is adjusted to pH 4 using sulfuric acid and extracted with toluene. The aqueous phase is discarded. The batch is then adjusted to pH 9 and extracted with toluene. The organic phase is discarded.

(c) (3→4): The aqueous solution obtained is stirred with completely deionized water to 5 liters and treated with catalytic amounts of Fe(III) chloride. Air is introduced until conversion is complete. The solution is adjusted to pH 2 and extracted with toluene. The phases are separated and the organic phase is concentrated. The residue is treated with technical grade heptane and forced through a filter loaded with 5 g of silica gel. R-Lipoic acid crystallizes with cooling and is dried in a stream of nitrogen.

The yield is 73% of theory with respect to diol 1
GC content: >99.9%
ee content: >99%

Example 9

Introduction of Sulfur

According to the processes such as have been described in Examples 1 to 8, sulfur can also be introduced into mesylates of compounds which contain the structural element (3).

The following table shows that disulfides can be introduced with good yields by the process according to the invention into various diols, for the synthesis of 4-membered, 5-membered or 6-membered rings. A good conversion was likewise achieved with 2,4-pentanediol in the mesylation and in the introduction of sulfur.

TABLE

| Diol | Yield of mesylate | Yield of disulfide |
| --- | --- | --- |
| (OH, OH diol structure) | 98% | 58% |
| (OH, OH, OH triol structure) | 76% | 40% |
| (OH, OH branched structure) | 100% | 85% |
| (OH, OH longer chain structure) | 100% | 56% |

The invention claimed is:

1. A solution containing sodium sulfide trihydrate and sulfur in methanol, the sulfur being present in a molar excess.

2. The solution as claimed in claim 1, the molar excess of sulfur over the sodium sulfide trihydrate being between 5 and 30%.

3. A kit comprising the solution as claimed in claim 1.

4. A process for the preparation of R- or S-dihydrolipoic acid comprising at least the step of a1) reacting a (S)-6,8-dihydroxyoctanoic acid derivative as shown in formula 2, (formula 2: structure with OMs, OMs and C(=O)O—R)

where

Ms is $SO_2$—R' and R and R' independently of one another are $C_1$–$C_6$-alkyl, $C_3$–$C_8$-cycloalkyl, $C_3$–$C_8$-cycloalkylalkyl, aryl or aralkyl with sodium sulfide and sulfur in methanol to give R-dihydrolipoic acid, or at least the step of a2) reacting the R-stereoisomer of the molecule shown in formula 2, with sodium sulfide and sulfur in methanol to give S-dihydrolipoic acid.

5. A process for the preparation of compounds containing the structural element (3)

(structural element 3)

m = 0, 1
n = 0, 1 comprising at least the step of reacting compound (4)

(structural element 4 with MsO, MsO)

m = 0, 1
n = 0, 1 with sodium sulfide trihydrate and sulfur in methanol.

6. The process as claimed in claim 4, the reaction being carried out with sodium sulfide trihydrate.

7. The process as claimed in claim 4, sulfur being present in a molar excess over the sodium sulfide.

8. The process as claimed in claim 4, wherein sodium sulfide trihydrate and sulfur in methanol is added to the (S)-6,8-dihydroxyoctanoic acid derivative as shown in formula 2 or to the respective (R) stereoisomer of the molecule shown in formula 2.

9. The process as claimed in claim 4, wherein the reaction temperature is between room temperature and 70° C.

10. The process as claimed in claim 9, wherein the reaction temperature is between 35 and 45° C.

11. The process for the preparation of R-lipoic acid or S-lipoic acid comprising the process step as described in claim 4 and F) subsequent oxidation of the R- or S-dihydrolipoic acid.

12. The process for the preparation of R-dihydrolipoic acid or dihydrolipoic acid comprising at lest step a1) or a2) as claimed in claim 4, wherein the R-dihydrolipoic acid or S-dihydrolipoic acid are chemically pure.

13. The process as claimed in claim 11, comprising the further processing of R-lipoic acid or S-lipoic acid into pharmacologically tolerable salts or derivatives.

14. A process for the production of cosmetics, of a pharmaceutical or pharmacon, comprising the step of claim 4, and g) formulation of the R-dihydrolipoic acid or S-dihydrolipoic acid in a dermatologically or pharmacologically tolerable form.

15. A process for the production of cosmetics, of a pharmaceutical or pharmacon comprising the step of claim 11, and h) formulation of the R-lipoic acid or S-lipoic acid in a dermatologically or pharmacologically tolerable form.

16. The process as claimed in claim 5, wherein the sulfur is present in a molar excess over the sodium sulfide.

17. The process as claimed in claim 5, wherein the reaction temperature is between room temperature and 70° C.

18. The process as claimed in claim 17, wherein the reaction temperature is between 35 and 45° C.

19. The process as claimed in claim 5, wherein the compounds containing the structural element (3) is chemically pure.

20. The process as claimed in claim 5, further comprising processing the compounds containing the structural element (3) into pharmacologically tolerable salts or derivatives.

* * * * *